(12) United States Patent
Gusyatiner et al.

(10) Patent No.: US 6,403,342 B1
(45) Date of Patent: Jun. 11, 2002

(54) DNA CODING FOR MUTANT ISOPROPYLMALATE SYNTHASE L-LEUCINE-PRODUCING MICROORGANISM AND METHOD FOR PRODUCING L-LEUCINE

(75) Inventors: Mikhail Markovich Gusyatiner; Maria Grigorievna Lunts; Yuly Ivanovich Kozlov; Lirina Valerievna Ivanovskaya; Elvira Borisovna Voroshilova, all of Moscow (RU)

(73) Assignee: Anjinomoto Co., Inc., Tokyo (JP)

( * ) Notice: Subject to any disclaimer, the term of this patent is extended or adjusted under 35 U.S.C. 154(b) by 0 days.

(21) Appl. No.: 09/612,964

(22) Filed: Jul. 10, 2000

(30) Foreign Application Priority Data

Jul. 9, 1999 (RU) .......................................... 99114325

(51) Int. Cl.[7] .............................. C12N 9/88; C12N 1/20; C12N 15/00; C12P 13/06; C07H 21/04

(52) U.S. Cl. ................. 435/116; 435/252.3; 435/320.1; 435/252.33; 435/232; 536/23.2

(58) Field of Search ............................... 435/232, 252.3, 435/320.1, 116, 252.33; 536/23.2

(56) References Cited

U.S. PATENT DOCUMENTS 5,744,331 A    4/1998   Nakano et al. ............. 435/116

FOREIGN PATENT DOCUMENTS

JP          62-34397         7/1987

*Primary Examiner*—Tekchand Saidha
(74) *Attorney, Agent, or Firm*—Oblon, Spivak, McClelland, Maier & Neustadt, P.C.

(57) ABSTRACT

A method for producing L-leucine, comprising the steps of: culturing a bacterium which is transformed with a DNA coding for an a-isopropylmalate synthase densensitized in feedback inhibition by L-leucine, in a culture medium to produce and accumulate L-leucine in the medium, and recovering L-leucine from the medium.

14 Claims, No Drawings

DNA CODING FOR MUTANT ISOPROPYLMALATE SYNTHASE L-LEUCINE-PRODUCING MICROORGANISM AND METHOD FOR PRODUCING L-LEUCINE

BACKGROUND OF THE INVENTION

Field of the Invention

The present invention relates to DNA coding for a mutant a-isopropylmalate synthase. Also, the present invention relates to an L-leucine-producing microorganism having the mutant a-isopropylmalate synthase, and a method for producing L-leucine by using the microorganism. L-Leucine is an essential amino acid which can be used as a nutritious additive for food or feed, reagents or materials for medical treatment, pharmaceutical or chemical industry, or a growth factor used for production of other amino acids, such as lysine.

Description of the Background

In the past, L-leucine has been produced by a method of fermentation primarily using microorganisms belonging to the genus Brevibacterium, Corynebacterium or Serratia or mutants thereof which produce L-leucine (Amino acid fermentation, JAPAN SCIENTIFIC SOCIETY'S PRESS, pp.397–422, 1986).

The highest level of L-leucine accumulation was obtained when using Brevibacterium flavum VKPM B-2736. This strain produces L-leucine at a concentration up to 26 g/L on sucrose-containing media for 72 h of fermentation in a laboratory fermenter (USSR Author Certificate 1394711). Moreover, *Brevibacterium lactofermentum* 34 is known to produce L-leucine up to 34 g/L on a medium with glucose (Appl. Environ. Microbiol. 51, p.1024 (1986)).

Although the productivity of L-leucine has been improved to some extent, the development of a more efficient and cost-effective method for producing L-leucine is necessary in order to meet the increasing demand for L-leucine.

On the other hand, microorganisms belonging to the genus Escherichia might be potentially utilized as a potent L-leucine-producing bacteria due to their rapid growth rate, prominent data obtained from genetic analysis and plentiful genetic materials. However, there are few reports which disclose the production of L-leucine using bacteria belonging to the genus Escherichia.

As L-leucine-producing bacterial strains of the genus Escherichia, a strain which is resistant to β-thienylalanine, β-hydroxyleucine (Japanese Patent Publication No. 62-34397 (1987) and a strain which is resistant to 4-azaleucine or 5,5,5-trifluoroleucine (Japanese Patent Application Laid-Open No. 8-70879 (1996)) are known.

However, neither L-leucine-resistant bacteria belonging to the genus Escherichia nor any relation between L-leucine resistance and productivity of L-leucine is known.

SUMMARY OF THE INVENTION

Accordingly, it is an object of the present invention to improve productivity of L-leucine of bacteria belonging to the genus Escherichia and to provide an efficient and cost-effective method for producing L-leucine.

It is, in particular, an object of the present invention to provide a DNA coding for a protein of the following (A) or (B):

(A) a protein having an amino acid sequence shown in SEQ ID NO:2 which has a substitution selected from the following (a) to (e):

(a) a substitution of another amino acid residue for a threonine residue at position 482, (b) a substitution of another amino acid residue for a glutamic acid residue at position 386, (c) a substitution of another amino acid residue for a proline residue at position 428, (d) a substitution of another amino acid residue for a glycine residue at position 479, and (e) a substitution of another amino acid residue for a glycine residue at position 462, (B) a protein having the amino acid sequence of the protein of (A), which sequence has deletion, substitution, insertion or addition of one or a few amino acid residues, the protein of (B) having α-isopropylmalate synthase activity and feedback inhibition of the activity by L-leucine being desensitized equivalently to that of the protein of (A).

It is, moreover, also an object of the present invention to provide a microorganism transformed with any of the the DNA defined above.

It is also an object of the present invention to provide a method of producing L- leucine.

The above objects and others are provided by a microorganism transformed with the DNA as defined above in (A)(a)–(e) and/or (B).

DETAILED DESCRIPTION OF THE PREFERRED EMBODIMENTS

The present inventors have surprisingly discovered that desensitization of feedback inhibition by L-leucine of α-isopropylmalate synthase (hereinafter abbreviated as IPMS) contributes to the production of L-leucine. The present invention is predicated upon this discovery.

Thus, the present invention provides a DNA coding for a protein of the following (A) or (B) (hereinafter also referred to as DNA of the present invention):

(A) a protein having an amino acid sequence shown in SEQ ID NO: 2 which has a substitution selected from the following (a) to (e):

(a) a substitution of another amino acid residue for a threonine residue at position 482, (b) a substitution of another amino acid residue for a glutamic acid residue at position 386, (c) a substitution of another amino acid residue for a proline residue at position 428, (d) a substitution of another amino acid residue for a glycine residue at position 479, and (e) a substitution of another amino acid residue for a glycine residue at position 462, (B) a protein having the amino acid sequence of the protein of (A), which sequence has deletion, substitution, insertion or addition of one or a few amino acid residues, said protein of (B) having α-isopropylmalate synthase activity and feedback inhibition of the activity by L-leucine being desensitized equivalently to that of the protein of (A).

The DNA of the present invention is preferably one in which the substitution is a substitution selected from the following (a') to (e'):

(a') a substitution of an isoleucine residue for a threonine residue at position 482, (b') a substitution of a lysine residue for a glutamic acid residue at position 386, (c') a substitution of a leucine residue for a proline residue at position 428, (d') a substitution of a cysteine residue for a glycine residue at position 479, and (e') a substitution of an aspartic acid residue for a glycine residue at position 462.

Specific examples of the DNA of the present invention include ones which has a nucleotide sequence shown in SEQ ID NO: 1, which sequence has a mutation selected from the following (i) to (v):

(i) a mutation of cytosine at position 1445 to thymine, (ii) a mutation of guanine at position 1156 to adenine, (iii) a mutation of cytosine at position 1283 to thymine, (iv) a mutation of guanine at position 1435 to thymine, and (v) a mutation of guanine at position 1385 to adenine.

The present invention also provides a microorganism which is transformed with the DNA of the present invention, and has an ability to produce L-leucine (hereinafter, also referred to as "microorganism of the present invention"). The microorganism of the present invention preferably belongs to the genus Escherichia. The microorganism of the present invention is more preferably Escherichia coli.

The present invention further provides a method for producing L-leucine, which entails:

culturing any one or more bacteria of the present invention in a culture medium to produce and accumulate L-leucine in the medium, and recovering L-leucine from the medium.

The present invention will be further explained below.

A. DNA of the present invention

The DNA of the present invention has a mutation to desensitize feedback inhibition by L-leucine of IPMS encoded by the DNA, in a DNA coding for a wild type IPMS.

The phrase "feedback inhibition by L-lysine is desensitized" means that the degree of the feedback inhibition is lowered. The lowering of the degree of feedback inhibition can be determined by measuring lowering of the IPMS activity by L-leucine and comparing it with that of wild strain or a parent strain.

IPMS is exemplified by those originating from bacteria belonging to the genus Escherichia, especially IPMS originating from *E. coli*. The mutation of IPS to desesitize feedback inhibition by L-leucine is exemplified by the following substitutions (a) to (e) in the amino acid sequence shown SEQ ID NO: 2:

(a) a substitution of another amino acid residue for a threonine residue at position 482, (b) a substitution of another amino acid residue for a glutamic acid residue at position 386, (c) a substitution of another amino acid residue for a proline residue at position 428, (d) a substitution of another amino acid residue for a glycine residue at position 479, and (e) a substitution of another amino acid residue for a glycine residue at position 462.

The substitutions preferably are the following (a') to (e')"

(a') a substitution of an isoleucine residue for a threonine residue at position 482, (b') a substitution of a lysine residue for a glutamic acid residue at position 386, (c') a substitution of a leucine residue for a proline residue at position 428, (d') a substitution of a cysteine residue for a glycine residue at position 479, and (e') a substitution of an aspartic acid residue for a glycine residue at position 462.

The DNA coding for the wild type IPMS is exemplified by one coding for IPMS originating from a bacterium belonging to the genus Escherichia. It is specifically exemplified by a DNA coding for an amino acid sequence shown in SEQ ID NO: 2, and is further specifically exemplified by a nucleotide sequence shown in SEQ ID NO: 1. In these sequences, those having the mutation in nucleotide sequence to cause the substitutions of amino acid residues described above are included in the DNA of the present invention. Any codon corresponding to the substituted amino acid residue is available irrelevantly to its kind, provided that it codes for the identical amino acid residue.

Specific examples of the DNA of the present invention include ones which has a nucleotide sequence shown in SEQ ID NO: 1, which sequence has a mutation selected from the following (i) to (v):

(i) a mutation of cytosine at position 1445 to thymine, (ii) a mutation of guanine at position 1156 to adenine, (iii) a mutation of cytosine at position 1283 to thymine, (iv) a mutation of guanine at position 1435 to thymine, and (v) a mutation of guanine at position 1385 to adenine.

Further, although a given IPMS may be slightly different in sequence from another depending on differences in bacterial species and bacterial strain, however, DNAs coding for those having replacement, deletion or insertion of amino acid residue(s) at position(s) irrelevant to the enzyme activity are also included in DNA of the present invention. In other words, a DNA coding for a protein having the amino acid sequence of the mutant IPMS, which sequence has deletion, substitution, insertion or addition of one or a few amino acid residues, said protein having an IPMS activity and feedback inhibition of the activity by L-leucine being desensitized equivalently to that of the mutant IPMS, is also specifically included in the DNA of the present invention. Such DNA includes those having mutations which may naturally occur, such as mutations based on differences between individuals, species and genera of microorganisms having IPMS (mutants or variants).

A method for obtaining a DNA coding for the mutant IPMS is as follows.

(1) Preparation of wild type IPMS gene

A donor microorganism for the DNA containing the wild type IPMS gene or the IPMS gene having another mutation described above, is preferably exemplified by a microorganism belonging to the genus Escherichia. Specifically, those described in a book written by Neidhardt et al. (Neidhardt, F. C. et al. , *Escherichia coli* and *Salmonella Typhimurium*, American Society for Microbiology, Washington D.C., 1208, table 1) may be used. For example, *E. coli* strains K-12, JM109, and MC1061 are exemplified. When a wild strain is used as a donor microorganism for a DNA containing a IPMS gene, a DNA containing a wild type IPMS gene can be obtained.

An example of preparation of a DNA containing a IPMS gene will be described below.

First, *E. coli* having wild type IPMS gene, for example, strain K-12, is cultivated to obtain a culture. When the microorganism described above is cultivated, cultivation may be performed in accordance with an ordinary solid culture method, however, cultivation is preferably performed by adopting a liquid culture method considering efficiency during collection of the bacterium. A medium may be used in which one or more nitrogen sources such as yeast extract, peptone, meat extract, corn steep liquor and exudate of soybean or wheat are added with one or more inorganic salts such as potassium dihydrogenphosphate, dipotassium hydrogenphosphate, magnesium sulfate, sodium chloride, magnesium chloride, ferric chloride, ferric sulfate or manganese sulfate, and further optionally and adequately added with sugar materials, vitamins and the like. It is appropriate that the initial pH of the medium is adjusted to 6 to 8. The cultivation is performed for 4 to 24 hours at 30 to 42° C., preferably at about 37° C. by means of deep culture with aeration and agitation, shaking culture or stationary culture or the like.

The culture thus obtained is centrifuged, for example, at 3,000 r.p.m. for 5 minutes to obtain a cell pellet of E. coli strain K-12. Chromosomal DNA can be obtained from the cell pellet by means of, for example, a method of Saito and Miura (Biochem. Biophys. Acta., 72, 619 (1963) ), or a method of K. S. Kirby (Biochem. J., 64, 405 (1956)).

In order to isolate the IPMS gene from the chromosomal DNA thus obtained, a chromosomal DNA library is prepared. At first, the chromosomal DNA is partially digested with a suitable restriction enzyme to obtain a mixture of various fragments. A wide variety of restriction enzymes can be used if the degree of cutting is controlled by the cutting reaction time and the like. For example, Sau3AI is allowed to react on the chromosomal DNA at a temperature not less than 30° C., preferably at 37° C. at an enzyme concentration of 1 to 10 units/ml for various periods of time (1 minute to 2 hours) to digest it.

Next, obtained DNA fragments are ligated with a vector DNA autonomously replicable in cells of bacteria belonging to the genus Escherichia to prepare recombinant DNA. Specifically, a restriction enzyme, which generates the terminal nucleotide sequence complement to that generated by the restriction enzyme Sau3AI used to cut the chromosomal DNA, for example, BamHI, is allowed to act on the vector DNA under a condition of a temperature not less than 30° C. and an enzyme concentration of 1 to 100 units/ml for not less than 1 hour, preferably for 1 to 3 hours to completely digest it, and cut and cleave it. Next, the chromosomal DNA fragment mixture obtained as described above is mixed with the cleaved and cut vector DNA, on which DNA ligase, preferably T4 DNA ligase is allowed to act under a condition of a temperature of 4 to 16° C. at an enzyme concentration of 1 to 100 units/ml for not less than I hour, preferably for 4 to 24 hours to obtain recombinant DNA.

The obtained recombinant DNA is used to transform a microorganism belonging to the genus Escherichia, for example, a IPMS deficient mutant strain such as an Escherichia coli strain K-12, preferably a strain JE7627 (ponB704, dacB12, pfv$^+$, tonA2, dapa, lysa, str, malA38, metbl, ilvH611, leuA371, proA3, lac-3, tsx-76) to prepare a chromosomal DNA library. The transformation can be performed, for example, by a method of D. M. Morrison (Methods in Enzymology 68, 326 (1979)) or a method in which recipient bacterial cells are treated with calcium chloride to increase permeability of DNA (Mandel, M. and Higa, A., J. Mol. Biol., 53, 159 (1970)). The strain JE7627 is available from National Institute of Genetics (Mishima-shi, Shizuoka-ken, Japan).

A bacterial strain having recombinant DNA of the IPMS gene is obtained from strains having increased IPMS activity or strains in which auxotrophy resulting from deficiency in the IPMS gene is complemented, among the obtained chromosomal DNA library. For example, a IPMS-deficient mutant strain requires L-leucine. Thus when the IPMS-deficient mutant strain is used as a host, a DNA fragment containing the IPMS gene can be obtained by isolating a bacterial strain which becomes capable of growing on a medium containing no L-leucine, and recovering recombinant DNA from the bacterial strain.

Confirmation of the fact whether or not a candidate strain having recombinant DNA containing a IPMS gene actually harbors recombinant DNA in which the IPMS gene is cloned can be achieved by preparing a cellular extract from the candidate strain, and preparing a crude enzyme solution therefrom to confirm whether or not the IPMS activity has been increased. A procedure to measure the enzyme activity of IPMS can be performed by a method of Kohlhaw et al. (J. Biol. Chem., 244, 2218(1969)).

Recombinant DNA in which the DNA containing the IPMS gene is inserted into the vector DNA can be isolated from the bacterial strain described above by means of, for example, a method of P. Guerry et al. (J. Bacteriol., 116, 1064 (1973) or a method of D. B. Clewell (J. Bacteriol., 110, 667 (1972)).

Preparation of the wild type IPMS gene can be also performed by preparing chromosomal DNA from a strain having a IPMS gene on chromosome by means of a method of Saito and Miura or the like, and amplifying the IPMS gene by means of a polymerase chain reaction (PCR) method (see White, T. J. et al.; Trends Genet., 5, 185(1989)). DNA primers to be used for the amplification reaction are those complemental to both 3'-terminals of a double stranded DNA containing an entire region or a partial region of the IPMS gene. When only a partial region of the IPMS gene is amplified, it is necessary to use such DNA fragments as primers to perform screening of a DNA fragment containing the entire region from a chromosomal DNA library. When the entire region of the IPMS gene is amplified, a PCR reaction solution including DNA fragments containing the amplified IPMS gene is subjected to agarose gel electrophoresis, and then an aimed DNA fragment is extracted. Thus a DNA fragment containing the IPMS gene can be recovered.

The DNA primers may be adequately prepared on the basis of, for example, a sequence known in E. coli (EMBL accession No. D10483 or AE000117). Specifically, primers which can amplify a region comprising 1572 nucleotides coding for the IPMS gene are preferable. Synthesis of the primers can be performed by an ordinary method such as a phosphoamidite method (see Tetrahedron Letters, 22, 1859 (1981) ) by using a commercially available DNA synthesizer (for example, DNA Synthesizer Model 380B produced by Applied Biosystems). Further, the PCR can be performed by using a commercially available PCR apparatus (for example, DNA Thermal Cycler Model PJ2000 produced by Takara Shuzo Co., Ltd., using Taq DNA polymerase (supplied by Takara Shuzo Co., Ltd.) in accordance with a method designated by the supplier.

With respect to the IPMS gene amplified by the PCR method, operations such as introduction of mutation into the IPMS gene become easy, when it is ligated with a vector DNA autonomously replicable in cells of bacteria belonging to the genus Escherichia, and introduced into cells of bacteria belonging to the genus Escherichia. The vector DNA to be used, the transformation method, and the confirmation method for the presence of the IPMS gene are the same as those in the aforementioned procedure. Reports on isolation of the IPMS gene include Hertberg, K. m. et al., Gene, 8, 135–152(1980), Davis, M. G. et al., J. Bacteriol., 129, 1078–1090(1977) for example.

The method for obtaining the IPMS gene as mentioned above may be used for obtaining mutant genes when a microorganism having a wild type IPMS is subjected to mutagenesis to produce a mutant strain producing a mutant IPMS and a mutant gene is obtained from the mutant strain.

(2) Introduction of mutation into IPMS gene

The method for carrying out mutation such as substitution, insertion and deletion of amino acid residues is exemplified by a recombinant PCR method (Higuchi, R., 61, in PCR Technology (Erlich, H. A. Eds., Stockton press (1989)), and a site specific mutagenes is method (Kramer, W. and Frits, H. J., Meth. in Enzymol., 154, 350 (1987); Kunkel T. A. et al., Meth. in Enzvmol., 154, 367 (1987)). Aimed mutation can be caused at an aimed site by using these methods.

Further, according to chemical synthesis of an aimed gene, it is possible to introduce mutation or random mutation into an aimed site.

Further, a method is available in which the IPMS gene on chromosome or plasmid is directly treated with hydroxylamine (Hashimoto, T. and Sekiguchi, M. J. Bacteriol., 159, 1039 (1984)). Alternatively, it is acceptable to use a method in which a bacterium belonging to the genus Escherichia having the IPMS gene is irradiated by ultraviolet light, or a method based on a treatment with a chemical agent such as N-methyl-N'-nitrosoguanidine or nitrous acid. According to these methods, mutation can be introduced randomly.

With respect to a selection method for the mutant gene, recombinant DNA comprising a DNA fragment containing the IPMS gene and vector DNA is at first directly subjected to a mutation treatment with hydroxylamine or the like, which is used to transform, for example, an E. coli strain W3110. Next, transformed strains are cultivated on a minimal medium such as M9 containing 4-aza-D,L-leucine or 3-hydroxy-D,L-leucine as an analog of L-leucine. Strains harboring recombinant DNA containing the wild type IPMS gene cannot synthesize L-leucine and are suppressed in growth because IPMS expressed from the recombinant DNA is inhibited by the analog of L-leucine. On the contrary, a strain harboring recombinant DNA containing the IPMS gene in which inhibition by L-leucine is desensitized has a mutant enzyme encoded by the IPMS gene in the aforementioned recombinant DNA which is not inhibited by the analog of L-leucine. Thus it should be capable of growth on the minimal medium in which the analog of L-leucine is added. This phenomenon can be utilized to select a strain which is resistant in growth to the analog of L-leucine, that is a strain harboring recombinant DNA containing a mutant IPMS gene in which inhibition is desensitized.

The mutant gene thus obtained may be introduced as a recombinant DNA into a suitable host microorganism, and expressed. Thus a microorganism can be obtained which harbors IPMS being desensitized to feedback inhibition. The host is preferably a microorganism belonging to the genus Escherichia, for which E. coli is exemplified.

Alternatively, a mutant IPMS gene fragment may be taken out from the recombinant DNA, and inserted into another vector to make use. The vector DNA which can be used in the present invention is preferably plasmid vector DNA, for which there are exemplified pUC19, pUC18, pBR322, pHSG299, pHSG298, pHSG399, pHSG398, RSF1010, pMW119, pMW118, pMW219 and pMW218. Besides, vectors of phage DNA can be also utilized.

Further, in order to express the mutant IPMS gene efficiently, another promoter which works in microorganisms such as lac, trp and PL may be ligated upstream from a DNA sequence coding for the mutant IPMS, or a promoter contained in the IPMS gene may be used as it is, or after amplifying the promoter.

In addition, as described above, the mutant gene may be inserted into an autonomously replicable vector DNA, which is inserted into a host, and allowed to be harbored by the host as extrachromosomal DNA such as a plasmid. Alternatively, the mutant gene may be integrated into chromosome of a host microorganism by a method using transduction, transposon (Berg, D. E. and Berg, C. M., Bio/Technol., 1, 417 (1983)), Mu phage (Japanese Patent Laid-open No. 2-109985) or homologous recombination (Experiments in Molecular Genetics, Cold Spring Harbor Lab. (1972)).

B. Microorganism of the present invention

The microorganism of the present invention is the microorganism which is transformed with the DNA of the present invention and has an ability to produce L-leucine.

The transformation by the DNA of the present invention may be carried out in accordance with conventional and known transformation methods. For example, a fragment including the DNA of the present invention is ligated with a vector which functions in a host (microorganism to be transformed) to prepare a recombinant DNA, and the recombinant DNA is introduced in the host. The vector may be suitably selected depending on the host. The introduction of the recombinant DNA in accordance with conventional and known methods. For example, it is possible to use a method in which recipient cells are treated with calcium chloride to increase permeability of DNA as reported for Escherichia coli K-12 (Mandel, M. and Higa, A., J. Mol. Biol., 53, 159 (1970)), and a method in which competent cells are prepared from cells at a proliferating stage to introduce DNA thereinto as reported for Bacillus subtilis (Duncan, C. H., Wilson, G. A. and Yound, F. E., Gene, 1, 153 (1977)). Alternatively, it is also possible to apply a method in which DNA recipient cells are converted into a state of protoplasts or spheroplasts which easily incorporate recombinant DNA to introduce recombinant DNA into DNA recipients as known for Bacillus subtilis, actinomycetes, and yeast (Chang, S and Choen, S. N., Molec. Gen. Genet., 168, 111 (1979); Bibb, M. J., Ward, J. M. and Hopwood, 0. A., Nature, 274, 398 (1978); Hinnen, A., Hicks, J. B. and Fink, G. R., Proc. Natl. Acad. Sci. USA, 75, 1929 (1978)). Also, an electric pulse method (Japanese Patent Application Laid-Open No. 2-207791 (1990) may be used. The introduction method may be suitably selected depending on the host. Specifically, the vector and the method are exemplified by those described in the above (A) (2).

The terms "having an ability to produce L-leucine" used herein means to accumulate L-leucine in a medium, preferably, in an amount such that L-leucine can be easily recovered from the medium.

The bacterium of the present invention preferably belongs to the genus Escherichia. It may be exemplified by Escherichia coli. A bacterium belonging to the genus Escherichia which has an ability to produce L-leucine is exemplified, for example, by bacteria having a resistance to leucine analog such as β-2-thienylalanine, 3-hydroxyleucine, 4-azaleucine and 5,5,5-trifluoroleucine, which are described in Japanese Patent Publication No. 62-34397 (1987) and Japanese Patent Application Laid-open No. 8-70879 (1996), and by bacterium which can be bred by genetic engineering techniques as described in WO96/06926.

In a bacterium belonging to the genus Escherichia, L-leucine is synthesized through biosynthetic pathway inherent to L-leucine which diverges from the final intermediate (2-ketoisovalerate) of L-valine biosynthesis system. In a bacterium belonging to the genus Escherichia, the final step of L-valine biosynthesis and biosynthesis inherent to L-leucine are carried out by a group of enzymes encoded by ilvGMEDA operon and those encoded by leuABCD operon, respectively.

The leuABCD operon includes leuA, leuB, leuC and leuD genes. Among them, leuA encodes IPMS, leuB encodes β-isopropylmalate dehydrogenase, leuC and leuD encodes isopropylmalate isomerase. Of these enzymes, IPMS catalyzes the synthetic reaction from α-ketoisovalerate to α-isopropylmalate, a-isopropylmalate isomerase catalyzes the isomerization reaction from β-isopropylmalate to α-isopropylmalate and β-isopropylmalate dehydrogenase catalyzes the dehydrogenation reaction from β-isopropylmalate to α-ketoisocaproic acid which is the final intermediate of L-leucine biosynthesis.

Of above-mentioned reactions in the L-leucine biosynthetic pathway, the rate determining step is the synthetic reaction from α-ketoisovalerate to α- isopropylmalate catalyzed by α-isopropylmalate synthase which suffers feedback inhibition by L-leucine. Therefore, transformation with the DNA coding for IPMS desensitized in the feedback inhibition can impart the ability to produce L-leucine to a microorganism or improve the ability to produce L-leucine of a microorganism.

The bacterium belonging to the genus Escherichia of the present invention may be enhanced in activity of one or more enzymes of L-leucine biosynthetic pathway by usual mutation treatment or genetic engineering techniques. Such an enhancement of the activity of the enzyme may be performed by introduction of recombinant DNA which is obtained by inserting a DNA fragment having an entire or a partial ilvGMEDA operon and/or leuABCD operon into a plasmid, phage or transposon to a bacterium belonging to the genus Escherichia.

The analysis of the nucleotide sequence of leuABCD operon was described in *Nucleic Acid Res.*, 20, 3305–3308 (1992). The entire sequence of leuABCD operon has been registered in the database (DDBJ accession no. D10483, Internet address of DDBJ: http://www.ddbj.nig.ac jp). A DNA fragment having leuABCD operon can be obtained by amplifying the DNA fragment in accordance with PCR (polymerase chain reaction, refer to White, T. J. et al., *Trends Genet.*, 5,185 (1989)) in which oligonucleotides prepared on the basis of the above described sequences are used as primers and chromosomal DNA of a bacterium belonging to the genus Escherichia is used as template for PCR. Alternatively, leuABCD operon can also be obtained by screening a chromosomal DNA library of a bacterium belonging to the genus Escherichia in accordance with hybridization by using an oligonucleotide probe prepared on the basis of the above described sequences.

The entire nucleotide sequence of ilvGMEDA operon and the nucleotide sequence of upstream region of the operon are described in *Nucleic Acid Res.*, 15, 2137–2155 (1987) and *Gene*, 97, 21–27 (1991), respectively. A DNA fragment having ilvGMEDA operon can be obtained by PCR or hybridization using oligonucleotide probe or primers prepared on the basis of the above described sequence. Incidentally, in the case of using *Escherichia coli* K-12 or its derivative to obtain ilvGMEDA operon, it is preferable to use a strain having a reverse mutation of ilvG gene in which the frame is restored so as to recover the activity of the acetohydroxy acid synthase. The methods for obtaining ilvGMEDA operon and the method for amplifying the operon in a cell of a bacterium belonging to the genus Escherichia are fully described in WO96/06926 and FR 2627508, respectively.

C. Method for producing L-leucine

L-Leucine can be efficiently produced by cultivating the bacterium which can be obtained as described above in a culture medium, producing and accumulating L-leucine in the medium, and recovering L-leucine from the medium.

In the method of present invention, the cultivation of the bacterium belonging to the genus Escherichia, the collection and purification of L-leucine from the liquid medium may be performed in a manner similar to the conventional fermentation method by which L-leucine is produced using a bacterium. A medium used in culture may be either a synthetic medium or a natural medium, so long as the medium includes a carbon and a nitrogen source and minerals and, if necessary, a suitable amount of nutrients which the bacterium used requires for growth. The carbon source may include one or more of various carbohydrates such as glucose and sucrose, and various organic acids. Regarding the mode of assimilation of the used bacterium, alcohol including ethanol and glycerol may be used. As the nitrogen source, it is possible to use various ammonium salts such as ammonia and ammonium sulfate, other nitrogen compounds such as amines, a natural nitrogen source such as peptone, soybean hydrolyte or digested fermentative microbe. As minerals, potassium phosphate, magnesium sulfate, sodium chloride, ferrous sulfate, manganese sulfate, or calcium carbonate may be used.

The cultivation is performed preferably under aerobic conditions such as a shaking culture, and an aeration and stirring culture, at a temperature of 20 to 40° C., preferably between 30 and 38° C. The pH of the culture is usually between 5 and 9, preferably between 6.5 and 7.2. The pH of the culture can be adjusted with ammonia, calcium carbonate, various acids, various bases, and buffers. Usually, cultivation for 1 to 3 days leads to the accumulation of the target L-leucine in the liquid medium.

After cultivation, insoluble substances such as cells are removed from the liquid medium by centrifugation and membrane filtration, and then the target L-leucine can be collected and purified by ionexchange, concentration and precipitation.

A microorganism of the present invention can be utilized as L-leucine producing strain or starting source for breeding of L-leucine producing strain. The present invention make it possible to produces L-leucine more efficiently in comparison with a formerly known method of producing L-leucine using a microorganism.

The present invention will now be further explained by reference to certain Examples, which are provided solely for purposes of illustration and are not intended to be limitative.

EXAMPLE 1

Obtaining of DNA Coding For Mutant IPMS a) Obtaining of L-leucine-producing strains The strains of *Escherichia coli*, producing L-leucine, were obtained from the standard laboratory wild-type strain *E. coli* K-12 by selection as described below. Cells of the strain *E. coli* K-12 were treated by solution of mutagen, containing 0.2 mg/ml N-methyl-N-nitro-N-nitrosoguanidine, for 30 min at 37° C. Then the cells were washed twice with NaCl solution (0.8%) and were spread on M9 agar medium dishes, containing 1 mg/ml of analog of L-leucine, 4-azaleucine. Colonies arisen after 5 days of incubation at 37° C. were picked up and the their capability of leucine production was tested. The strains No. 9, No. 68, No. 58, No. 55, and No. 15 produced L-leucine.

b) Obtaining of leua gene from L-leucine-producing strains

The leuA gene of the obtained leucine-producing mutant No. 55 and that of the wild-type strain *E. coli* K-12 were cloned by the in vivo cloning method using defective bacteriophage Mu d5005 (Groisman, E. A. et al., *J. Bacteriol.*, 168, 357 (1986)). Then overlapping fragments of thus cloned leua gene were amplified by means of the PCR method, using the DNA primers, LeuA1 and LeuA2, LeuA3 and LeuA4, LeuA5 and LeuA6, LeuA7 and LeuA8, and LeuA9 and LeuA10, respectively, shown in Table 1.

TABLE 1

Primers used for PCR

| N | Structure (5'—>3') | SEQ ID NO. |
|---|---|---|
| LeuA1 | ccaataccgtcccccggc | 3 |
| LeuA2 | ggtgaaatacagcctgacc | 4 |
| LeuA3 | gtgatgcggttaattgcctg | 5 |
| LeuA4 | tgacctctcgttcggggcgt | 6 |
| LeuA5 | gattcagctggatttggttc | 7 |
| LeuA6 | cgacgatttgggcctggcg | 8 |
| LeuA7 | ggcatgtaccgccgccagtga | 9 |
| LeuA8 | gaagccttccgtattcatacc | 10 |
| LeuA9 | cagcttggtggcgatgtgc | 11 |
| LeuA10 | gcccgaagcgaggcgctc | 12 |

The same DNA primers were used for amplification of the leuA genes from the chromosomes of the strains No. 9, No.

68, No. 58, and No. 15 without preliminarily cloning. The nucleotide sequences of the fragments were determined by dideoxy chain termination method.

The leuA genes from the strains No. 9, No. 68, No. 58, No. 55, and No. 15 contained mutations, indicated in the Table 2.

Cells of the strains were grown for 10 hours at 32° C. in the medium containing glucose (6%), ammonium sulfate (1.5%), potassium dihydrophosphate (0.2%), magnesium sulfate (0.1%), chalk (2.5%), and thiamine (0.1 mg/l). Cell-free extracts were obtained by sonication and ammonia sulfate precipitation was used as an enzyme preparation. Specific IPMS activity was determined by the method of Kohlhaw et al. (*J. Biol. Chem.*, 244, 2218 (1969)). $I_{50}$ is a leucine concentration which causes 50% inhibition of the enzyme activity. L-Leucine production was determined after 48 hours of cultivation in the medium indicated The results are summarized in Table 2.

TABLE 2

Properties of the L-leucine-producing mutants

| Strain | Substitution of amino acid (Substitution of nucleotide) | IPMS Specific Activity (nmol/min/mg protein) | $I_{50}$ (mM) | Leucine production (g/l) |
|---|---|---|---|---|
| K-12 (wild) | None (none) | 9 | 0.2 | 0.0 |
| 9 | $Thr_{482} \rightarrow Ile$ ($C_{1445} \rightarrow T$) | 25 | 1.4 | 0.8 |
| 68 | $Glu_{386} \rightarrow Lys$ ($G_{1156} \rightarrow A$) | 21 | 1.4 | 2.3 |
| 58 | $Pro_{428} \rightarrow Leu$ ($C_{1283} \rightarrow T$) | 29 | 2.5 | 1.0 |
| 55 | $Gly_{479} \rightarrow Cys$ ($G_{1435} \rightarrow T$) | 10 | 8.2 | 5.2 |
| 15 | $Gly_{462} \rightarrow Asp$ ($G_{1385} \rightarrow A$) | 9 | >10.0 | 1.0 |

EXAMPLE 2

Production Of L-leucine By Transformants

*E. coli* C600 (leu⁻) (Appleyard R. K., *Genetics*, 39, 440–452 (1954)) was transduced by P1 phages grown on leucine-producing strains No. 9, No. 68, No. 58, No. 55 and No. 15, and *E. coli* K-12. Leu⁺ transductants were obtained and tested for the ability to produce L-leucine. The data are present in Table 3.

TABLE 3

Production of L-leucine by transductants

| Donor strain | Leucine production* (g/l) |
|---|---|
| *E. coli* K-12 | 0 |
| 9 | 0.55 |
| 68 | 0.6 |
| 58 | 0.3 |
| 15 | 1.0 |
| 55 | 1.3 |

*L-Leucine production was determined after 48 hours of cultivation at 32° C. The data of production present average of 10 transductants of each type.

*L-Leucine production was determined after 48 hours of cultivation at 32° C. The data of production present average of 10 transductants of each type.

Having described the present invention, it will now be apparent that many changes and modifications may be made to the above-described embodiments without departing from the spirit and scope of the present invention.

What is claimed is:

1. An isolated DNA comprising (A) or (B): wherein,
   (A) a DNA coding for a protein having α-isopropylmate synthase activity and an amino acid sequence shown in SEQ ID NO: 2 which has a substitution selected from the following (a) to (e):
   (a) a substitution of another amino acid residue for a threonine residue at position 482,
   (b) a substitution of another amino acid residue for a glutamic acid residue at position 386,
   (c) a substitution of another amino acid residue for a proline residue at position 428,
   (d) a substitution of another amino acid residue for a glycine residue at position 479, and
   (e) a substitution of another amino acid residue for a glycine residue at position 462,
   (B) a DNA obtained by subjecting the DNA of (A) to mutagenesis and selecting a DNA coding for a protein having an α-isopropylmalate synthase activity and feedback inhibition of the activity by L-leucine being desensitized equivalently to that of the protein encoded by the DNA of (A).

2. The DNA of claim 1, wherein said substitution is selected from the following (a') to (e'):
   (a') a substitution of an isoleucine residue for a threonine residue at position 482,
   (b') a substitution of a lysine residue for a glutamic acid residue at position 386,
   (c') a substitution of a leucine residue for a proline residue at position 428,
   (d') a substitution of a cysteine residue for a glycine residue at position 479, and
   (e') a substitution of an aspartic acid residue for a glycine residue at position 462.

3. The DNA of claim 2, which has a nucleotide sequence shown in SEQ ID NO: 1, which sequence has a mutation selected from the following (i) to (v):
   (i) a mutation of cytosine at position 1445 to thymine,
   (ii) a mutation of guanine at position 1156 to adenine,
   (iii) a mutation of cytosine at position 1283 to adenine,
   (iv) a mutation of guanine at position 1435 to thymine, and
   (v) a mutation of guanine at position 1385 to adenine.

4. A microorganism which is transformed with the DNA of claim 1, and produces L-leucine.

5. The microorganism of claim 4, which belongs to the genus Escherichia.

6. The microorganism of claim 5, which is *Escherichia coli*.

7. The microorganism of claim 5, which produces at least 0.8 g/l of L-leucine.

8. The microorganism of claim 7, which produces at least 1.0 g/l of L-leucine.

9. A method for producing L-leucine, comprising:
   a) culturing the microorganism of claim 4 in a culture medium, thereby producing and accumulating L-leucine in the medium; and
   b) recovering L-leucine from the medium.

10. The method of claim 9, wherein said culturing is effected under aerobic conditions.

11. The method of claim 9, wherein said culturing is effected at 20 to 40° C.

12. The method of claim 11, wherein said culturing is effected at 30 to 38° C.

13. The method of claim 9, wherein said culturing is conducted at a pH of 5 to 9.

14. The method of claim 13, wherein said culturing is conducted at a pH of 6.5 to 7.2.

* * * * *

UNITED STATES PATENT AND TRADEMARK OFFICE
CERTIFICATE OF CORRECTION

PATENT NO. : 6,403,342 B1
DATED : June 11, 2002
INVENTOR(S) : Mikhail Markovich Gusyatiner et al.

It is certified that error appears in the above-identified patent and that said Letters Patent is hereby corrected as shown below:

Column 22,
Line 33, "adenine" should read -- thymine --.

Signed and Sealed this

Twenty-fifth Day of January, 2005

JON W. DUDAS
*Director of the United States Patent and Trademark Office*

SEQUENCE LISTING

<160> NUMBER OF SEQ ID NOS: 12

<210> SEQ ID NO 1
<211> LENGTH: 1572
<212> TYPE: DNA
<213> ORGANISM: Escherichia coli
<220> FEATURE:
<221> NAME/KEY: CDS
<222> LOCATION: (1)..(1569)

<400> SEQUENCE: 1

```
atg agc cag caa gtc att att ttc gat acc a ca ttg cgc gac ggt gaa        48
Met Ser Gln Gln Val Ile Ile Phe Asp Thr T hr Leu Arg Asp Gly Glu
  1               5                  10                  15 cag gcg tta cag gca agc ttg agt gtg aaa g aa aaa ctg caa att gcg        96
Gln Ala Leu Gln Ala Ser Leu Ser Val Lys G lu Lys Leu Gln Ile Ala
             20                  25                  30 ctg gcc ctt gag cgt atg ggt gtt gac gtg a tg gaa gtc ggt ttc ccc       144
Leu Ala Leu Glu Arg Met Gly Val Asp Val M et Glu Val Gly Phe Pro
         35                  40                  45 gtc tct tcg ccg ggc gat ttt gaa tcg gtg c aa acc atc gcc cgc cag       192
Val Ser Ser Pro Gly Asp Phe Glu Ser Val G ln Thr Ile Ala Arg Gln
     50                  55                  60
```

```
gtt aaa aac agc cgc gta tgt gcg tta gct c gc tgc gtg gaa aaa gat      240
Val Lys Asn Ser Arg Val Cys Ala Leu Ala A rg Cys Val Glu Lys Asp
 65                  70                  75                  80 atc gac gtg gcg gcc gaa tcc ctg aaa gtc g cc gaa gcc ttc cgt att      288
Ile Asp Val Ala Ala Glu Ser Leu Lys Val A la Glu Ala Phe Arg Ile
                 85                  90                  95 cat acc ttt att gcc act tcg cca atg cac a tc gcc acc aag ctg cgc      336
His Thr Phe Ile Ala Thr Ser Pro Met His I le Ala Thr Lys Leu Arg
            100                 105                 110 agc acg ctg gac gag gtg atc gaa cgc gct a tc tat atg gtg aaa cgc      384
Ser Thr Leu Asp Glu Val Ile Glu Arg Ala I le Tyr Met Val Lys Arg
        115                 120                 125 gcc cgt aat tac acc gat gat gtt gaa ttt t ct tgc gaa gat gcc ggg      432
Ala Arg Asn Tyr Thr Asp Asp Val Glu Phe S er Cys Glu Asp Ala Gly
130                 135                 140 cgt aca ccc att gcc gat ctg gcg cga gtg g tc gaa gcg gcg att aat      480
Arg Thr Pro Ile Ala Asp Leu Ala Arg Val V al Glu Ala Ala Ile Asn
145                 150                 155                 160 gcc ggt gcc acc acc atc aac att ccg gac a cc gtg ggc tac acc atg      528
Ala Gly Ala Thr Thr Ile Asn Ile Pro Asp T hr Val Gly Tyr Thr Met
                165                 170                 175 ccg ttt gag ttc gcc gga atc atc agc ggc c tg tat gaa cgc gtg cct      576
Pro Phe Glu Phe Ala Gly Ile Ile Ser Gly L eu Tyr Glu Arg Val Pro
            180                 185                 190 aac atc gac aaa gcc att atc tcc gta cat a cc cac gac gat ttg ggc      624
Asn Ile Asp Lys Ala Ile Ile Ser Val His T hr His Asp Asp Leu Gly
        195                 200                 205 ctg gcg gtc gga aac tca ctg gcg gcg gta c at gcc ggt gca cgc cag      672
Leu Ala Val Gly Asn Ser Leu Ala Ala Val H is Ala Gly Ala Arg Gln
210                 215                 220 gtg gaa ggc gca atg aac ggg atc ggc gag c gt gcc gga aac tgt tcc      720
Val Glu Gly Ala Met Asn Gly Ile Gly Glu A rg Ala Gly Asn Cys Ser
225                 230                 235                 240 ctg gaa gaa gtc atc atg gcg atc aaa gtt c gt aag gat att ctc aac      768
Leu Glu Glu Val Ile Met Ala Ile Lys Val A rg Lys Asp Ile Leu Asn
                245                 250                 255 gtc cac acc gcc att aat cac cag gag ata t gg cgc acc agc cag tta      816
Val His Thr Ala Ile Asn His Gln Glu Ile T rp Arg Thr Ser Gln Leu
            260                 265                 270 gtt agc cag att tgt aat atg ccg atc ccg g ca aac aaa gcc att gtt      864
Val Ser Gln Ile Cys Asn Met Pro Ile Pro A la Asn Lys Ala Ile Val
        275                 280                 285 ggc agc ggc gca ttc gca cac tcc tcc ggt a ta cac cag gat ggc gtg      912
Gly Ser Gly Ala Phe Ala His Ser Ser Gly I le His Gln Asp Gly Val
290                 295                 300 ctg aaa aac cgc gaa aac tac gaa atc atg a ca cca gaa tct att ggt      960
Leu Lys Asn Arg Glu Asn Tyr Glu Ile Met T hr Pro Glu Ser Ile Gly
305                 310                 315                 320 ctg aac caa atc cag ctg aat ctg acc tct c gt tcg ggg cgt gcg gcg     1008
Leu Asn Gln Ile Gln Leu Asn Leu Thr Ser A rg Ser Gly Arg Ala Ala
                325                 330                 335 gtg aaa cat cgc atg gat gag atg ggg tat a aa gaa agt gaa tat aat     1056
Val Lys His Arg Met Asp Glu Met Gly Tyr L ys Glu Ser Glu Tyr Asn
            340                 345                 350 tta gac aat ttg tac gat gct ttc ctg aag c tg gcg gac aaa aaa ggt     1104
Leu Asp Asn Leu Tyr Asp Ala Phe Leu Lys L eu Ala Asp Lys Lys Gly
        355                 360                 365 cag gtg ttt gat tac gat ctg gag gcg ctg g cc ttc atc ggt aag cag     1152
Gln Val Phe Asp Tyr Asp Leu Glu Ala Leu A la Phe Ile Gly Lys Gln
```

```
                    370              375              380
caa gag gag ccg gag cat ttc cgt ctg gat t ac ttc agc gtg cag tct      1200
Gln Glu Glu Pro Glu His Phe Arg Leu Asp T yr Phe Ser Val Gln Ser
385                     390                  395                 400 ggc tct aac gat atc gcc acc gcc gcc gtc a aa ctg gcc tgt ggc gaa      1248
Gly Ser Asn Asp Ile Ala Thr Ala Ala Val L ys Leu Ala Cys Gly Glu
                405                  410                 415 gaa gtc aaa gca gaa gcc gcc aac ggt aac g gt ccg gtc gat gcc gtc      1296
Glu Val Lys Ala Glu Ala Ala Asn Gly Asn G ly Pro Val Asp Ala Val
            420                  425                 430 tat cag gca att aac cgc atc act gaa tat a ac gtc gaa ctg gtg aaa      1344
Tyr Gln Ala Ile Asn Arg Ile Thr Glu Tyr A sn Val Glu Leu Val Lys
                435                  440                 445 tac agc ctg acc gcc aaa ggc cac ggt aaa g at gcg ctg ggt cag gtg      1392
Tyr Ser Leu Thr Ala Lys Gly His Gly Lys A sp Ala Leu Gly Gln Val
            450                  455                 460 gat atc gtc gct aac tac aac ggt cgc cgc t tc cac ggc gtc ggc ctg      1440
Asp Ile Val Ala Asn Tyr Asn Gly Arg Arg P he His Gly Val Gly Leu
465                 470                  475                 480 gct acc gat att gtc gag tca tct gcc aaa g cc atg gtg cac gtt ctg      1488
Ala Thr Asp Ile Val Glu Ser Ser Ala Lys A la Met Val His Val Leu
                485                  490                 495 aac aat atc tgg cgt gcc gca gaa gtc gaa a aa gag ttg caa cgc aaa      1536
Asn Asn Ile Trp Arg Ala Ala Glu Val Glu L ys Glu Leu Gln Arg Lys
            500                  505                 510 gct caa cac aac gaa aac aac aag gaa acc g tg tga                      1572
Ala Gln His Asn Glu Asn Asn Lys Glu Thr V al
                515                  520

<210> SEQ ID NO 2
<211> LENGTH: 523
<212> TYPE: PRT
<213> ORGANISM: Escherichia coli

<400> SEQUENCE: 2

Met Ser Gln Gln Val Ile Ile Phe Asp Thr T hr Leu Arg Asp Gly Glu
 1               5                  10                  15

Gln Ala Leu Gln Ala Ser Leu Ser Val Lys G lu Lys Leu Gln Ile Ala
            20                  25                  30

Leu Ala Leu Glu Arg Met Gly Val Asp Val M et Glu Val Gly Phe Pro
        35                  40                  45

Val Ser Ser Pro Gly Asp Phe Glu Ser Val G ln Thr Ile Ala Arg Gln
    50                  55                  60

Val Lys Asn Ser Arg Val Cys Ala Leu Ala A rg Cys Val Glu Lys Asp
65                  70                  75                  80

Ile Asp Val Ala Ala Glu Ser Leu Lys Val A la Glu Ala Phe Arg Ile
                85                  90                  95

His Thr Phe Ile Ala Thr Ser Pro Met His I le Ala Thr Lys Leu Arg
            100                 105                 110

Ser Thr Leu Asp Glu Val Ile Glu Arg Ala I le Tyr Met Val Lys Arg
        115                 120                 125

Ala Arg Asn Tyr Thr Asp Asp Val Glu Phe S er Cys Glu Asp Ala Gly
    130                 135                 140

Arg Thr Pro Ile Ala Asp Leu Ala Arg Val V al Glu Ala Ala Ile Asn
145                 150                 155                 160

Ala Gly Ala Thr Thr Ile Asn Ile Pro Asp T hr Val Gly Tyr Thr Met
                165                 170                 175
```

```
            -continued

Pro Phe Glu Phe Ala Gly Ile Ile Ser Gly Leu Tyr Glu Arg Val Pro
        180                 185                 190

Asn Ile Asp Lys Ala Ile Ile Ser Val His Thr His Asp Leu Gly
    195                 200                 205

Leu Ala Val Gly Asn Ser Leu Ala Ala Val His Ala Gly Ala Arg Gln
210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
    290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Gly Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
ccaataccgt cccccggc                                                    18
```

```
<210> SEQ ID NO 4
<211> LENGTH: 19
<212> TYPE: DNA
<213> ORGANISM: Artificial Sequence
<220> FEATURE:
<223> OTHER INFORMATION: Synthetic DNA

<400> SEQUENCE: 4
ggtgaaatac agcctgacc                                              19

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
gtgatgcggt taattgcctg                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
tgacctctcg ttcggggcgt                                             20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
gattcagctg gatttggttc                                             20

<210> SEQ ID NO 8
<211> LENGTH: 19
<212> TYPE: DNA
<213> ORGANISM: Artificial Sequence
<220> FEATURE:
<223> OTHER INFORMATION: Synthetic DNA

<400> SEQUENCE: 8
cgacgatttg ggcctggcg                                              19

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
ggcatgtacc gccgccagtg a                                           21

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA
```

```
<400> SEQUENCE: 10
gaagccttcc gtattcatac c                                             21

<210> SEQ ID NO 11
<211> LENGTH: 19
<212> TYPE: DNA
<213> ORGANISM: Artificial Sequence
<220> FEATURE:
<223> OTHER INFORMATION: Synthetic DNA

<400> SEQUENCE: 11
cagcttggtg gcgatgtgc                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic DNA

<400> SEQUENCE: 12
gcccgaagcg aggcgctct                                                19
       -1-
```